(12) United States Patent
Hunter et al.

(10) Patent No.: US 12,193,748 B2
(45) Date of Patent: Jan. 14, 2025

(54) EYE ACCOMMODATION CONTROL

(71) Applicant: Welch Allyn, Inc., Skaneateles Falls, NY (US)

(72) Inventors: Vivian L. Hunter, Skaneateles Falls, NY (US); David L. Kellner, Baldwinsville, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 474 days.

(21) Appl. No.: 17/649,575

(22) Filed: Feb. 1, 2022

(65) Prior Publication Data

US 2022/0248954 A1    Aug. 11, 2022

Related U.S. Application Data

(60) Provisional application No. 63/147,904, filed on Feb. 10, 2021.

(51) Int. Cl.
*A61B 3/14*     (2006.01)
*G06T 7/00*    (2017.01)

(52) U.S. Cl.
CPC .............. *A61B 3/14* (2013.01); *G06T 7/0012* (2013.01); *G06T 2207/30041* (2013.01)

(58) Field of Classification Search
CPC ......... A61B 3/14; A61B 3/103; G06T 7/0012; G06T 2207/30041
USPC ........................................ 351/200, 205, 206
See application file for complete search history.

(56) References Cited

U.S. PATENT DOCUMENTS

| | | | |
|---|---|---|---|
| 4,778,268 A | 10/1988 | Randle | |
| 7,490,940 B2* | 2/2009 | Lai | A61B 3/1015 351/205 |
| 7,963,654 B2 | 6/2011 | Aggarwala | |
| 8,403,480 B2 | 3/2013 | Chen et al. | |
| 9,237,846 B2 | 1/2016 | Mowrey et al. | |
| 9,408,535 B2 | 8/2016 | Mowrey et al. | |
| 10,345,590 B2 | 7/2019 | Samec et al. | |
| 10,451,895 B2 | 10/2019 | Macnamara et al. | |
| 10,588,507 B2 | 3/2020 | Skolianos et al. | |
| 10,702,147 B2 | 7/2020 | Lane et al. | |
| 2012/0212598 A1 | 8/2012 | Mowrey et al. | |
| 2018/0160899 A1 | 6/2018 | Brown et al. | |
| 2020/0121185 A1 | 4/2020 | Lee et al. | |
| 2020/0245861 A1 | 8/2020 | Oberheide et al. | |

FOREIGN PATENT DOCUMENTS

| | | |
|---|---|---|
| CN | 109276422 A | 1/2019 |
| GB | 290527 A | 5/1928 |

OTHER PUBLICATIONS

Cholewiak, Steven A. et al., "Creating correct blur and its effect on accommodation," Journal of Vision, Sep. 2018, vol. 18, 1, Copyright 2018 The Authors, 54 pages.
(Continued)

*Primary Examiner* — Tuyen Tra
(74) *Attorney, Agent, or Firm* — Merchant & Gould P.C.

(57) ABSTRACT

A vision screening device includes an image capture component. The vision screening device displays a chromatic aberration, captures an optical image using the image capture component, and estimates a refractive error based on the optical image.

15 Claims, 7 Drawing Sheets

(56) References Cited

OTHER PUBLICATIONS

Gibaldi, Agostino et al., "Modeling Accommodation Control of the Human Eye: Chromatic Aberration and Color Opponency," University of California, Berkeley, Apr. 3, 2017, 1 page.

Kruger, Philip et al., "Small Amounts of Chromatic Aberration Influence Dynamic Accommodation," Optometry and Vision Science, Copyright © 1995 American Academy of Optometry, vol. 72, No. 9, pp. 656-668.

Cholewiak, Steven A. et al., "ChromaBlur: Rendering Chromatic Eye Aberration Improves Accommodation and Realism," ACM Transactions on Graphics, vol. 36, No. 6, Article 210. Publication Date: Nov. 2017, 12 pages.

Welch Allyn® Spot®, "Vision Screener Model VS100" Directions for use, Software version 3.0.XX, Instruction Manual, 56 pages.

Extended European Search Report for Application No. 22155435.5 mailed Jul. 12, 2022.

\* cited by examiner

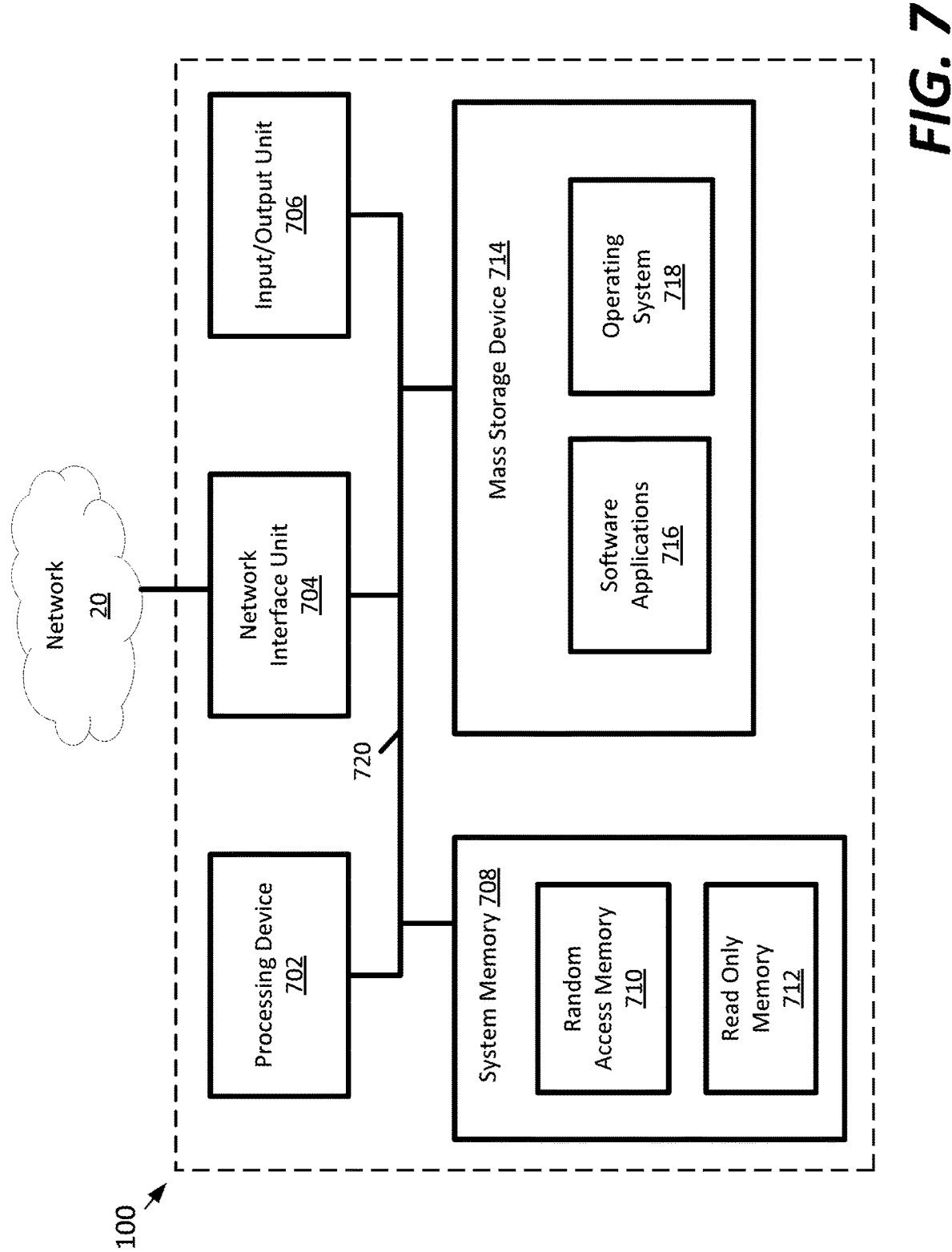

EYE ACCOMMODATION CONTROL

BACKGROUND

A vision screener is an instrument that can help identify refractive errors and ocular misalignments by detecting light reflexes from each eye during screening. Vision screeners evaluate the light reflexes from the retina to estimate refractive error. Vision screeners may also estimate pupil size, pupil distance, and eye gaze deviation. Typically, vision screeners are handheld devices, and are intended for use on pediatric subjects.

SUMMARY

In general terms, the present disclosure relates to reducing eye accommodation during vision screening. In one possible configuration, a chromatic aberration is displayed to reduce eye accommodation during capture of an optical image. Various aspects are described in this disclosure, which include, but are not limited to, the following aspects.

In one aspect, a vision screening device comprises: an image capture component; at least one processing device operatively connected to the image capture component; and at least one computer readable data storage device storing software instructions that, when executed by the at least one processing device, cause the vision screening device to: display a chromatic aberration; capture an optical image using the image capture component; and estimate a refractive error based on the optical image.

In another aspect, a method of vision screening comprises: displaying a chromatic aberration; capturing an optical image during the display of the chromatic aberration; and estimating a refractive error of one or more eyes based on the optical image.

In another aspect, a computer-readable data storage medium comprises software instructions that, when executed, cause at least one computing device to: display a chromatic aberration; capture an optical image during the display of the chromatic aberration; and estimate a refractive error of one or more eyes based on the optical image.

DESCRIPTION OF THE FIGURES

The following drawing figures, which form a part of this application, are illustrative of the described technology and are not meant to limit the scope of the disclosure in any manner.

FIG. 7 schematically illustrates components of the vision screening device of FIG. 1.

DETAILED DESCRIPTION

In general terms, the present disclosure relates to reducing eye accommodation during vision screening. In one possible configuration, a chromatic aberration is displayed to reduce eye accommodation during capture of an optical image.

Eye accommodation is the mechanism by which the eye changes optical power to maintain a clear image or focus on an object as its distance varies. Distances vary from the far point, the maximum distance from the eye for which a clear image of an object can be seen, to the near point, the minimum distance for a clear image. Eye accommodation is achieved by the eye lens changing its shape. Children are able to accommodate their eyes more quickly, for a longer duration of time, and to a higher degree than older adults. This is because children typically have softer and more flexible eye lenses that can more easily accommodate.

Figure 1:
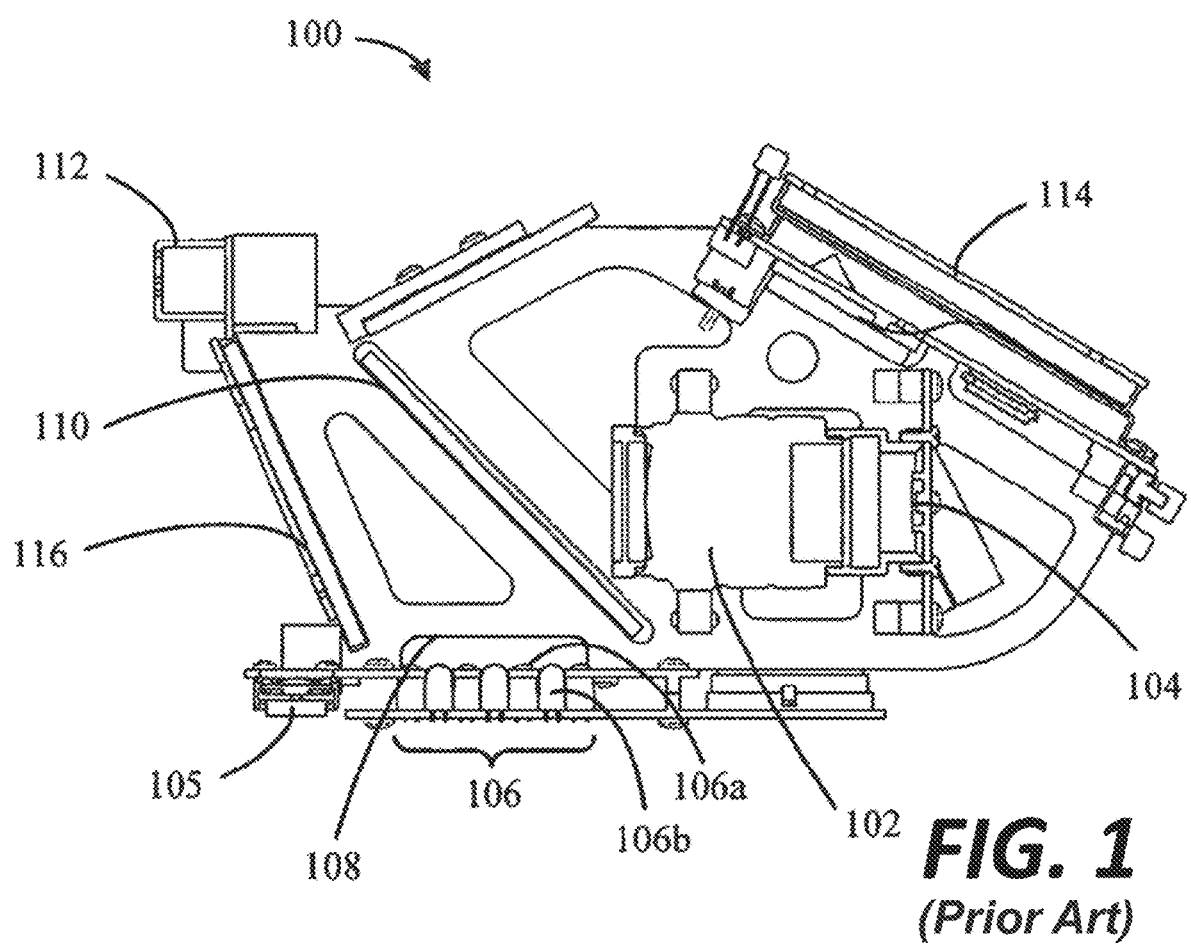
FIG. 1 is a cross-sectional view of an example of a vision screening device.
Figure 2:
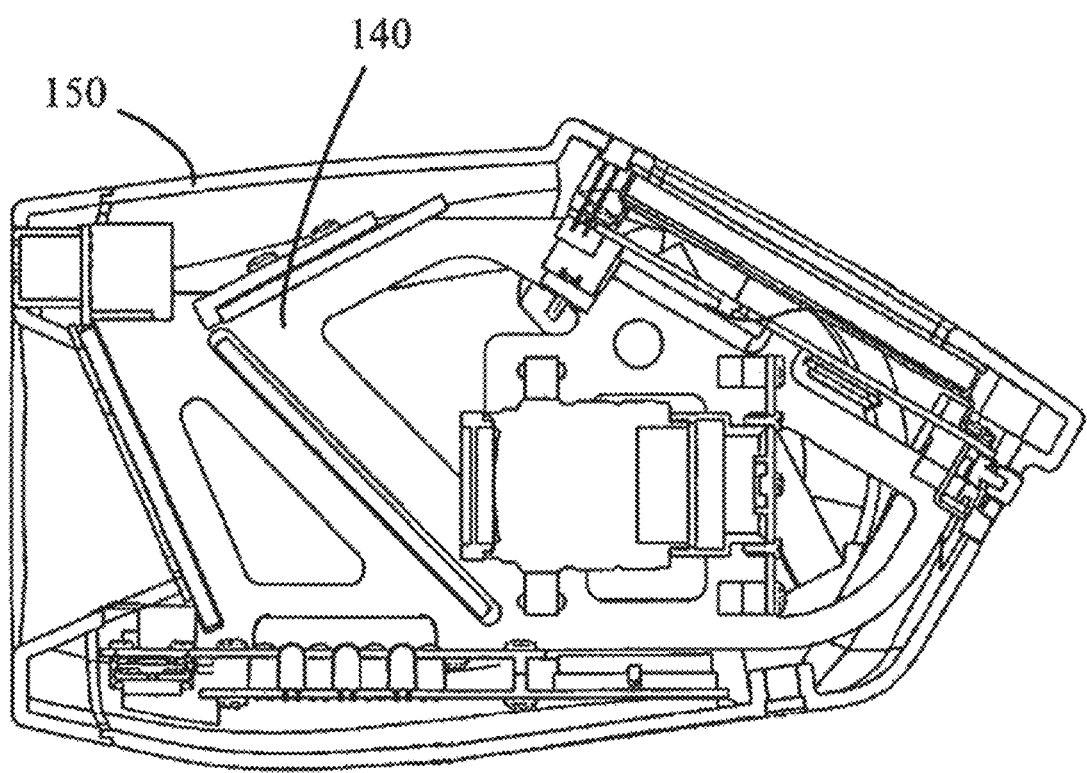
FIG. 2 is another cross-sectional view of the vision screening device of FIG. 1.

FIGS. 1 and 2 illustrate cross-sectional views of an exemplary embodiment of a vision screening device 100 for conducting an ocular examination on an examinee. Components of the vision screening device 100 are identified and described with reference to FIG. 1, while FIG. 2 further illustrates a frame 140 enclosed within a housing 150 of the vision screening device 100 for supporting the components shown in FIG. 1. In certain aspects, these components are similar to the components described in U.S. Pat. No. 9,237,846 issued on Jan. 19, 2016, the entirety of which is hereby incorporated by reference.

Referring to FIG. 1, the vision screening device 100 includes optical and non-optical components. The optical components may include a lens component 102 coupled to an image capture component 104, a light-emitting diode (LED) array 106 having visible LEDs 106a and near-infrared (NIR) LEDs 106b, a holographic diffuser 108, and a beam-splitter 110. The non-optical components may include a speaker 105, a range finder 112, an operator display screen 114, and a front window 116. It should be noted that vision screening device 100 is not limited to the foregoing listed components and may incorporate additional components, as needed.

The vision screening device 100 is preferably configured for mobility, but may also be suitable for stationary applications. Additionally, the vision screening device 100 may be wirelessly enabled to permit image data collection and analysis to be transmitted to a remote location for printing a report or to permit further assessment of an examinee's ocular response. For example, upon conducting an ocular examination using the vision screening device 100, image data collected and corresponding results may be wirelessly transmitted and stored in a remote patient database configured for accessibility by authorized medical professionals.

The vision screening device 100 has functionality driven by a plurality of processes configured to assess ocular aspects of an examinee including, but not limited to, presenting attention-getting stimuli to the examinee, controlling an LED arrangement to irradiate pupils of the examinee, locating pupils of the examinee in captured images, displaying captured images to an operator, and analyzing pupil image data for determining refractive error and conducting related assessments. These processes may be performed by processing logic (not shown) under computer program control in the vision screening device 100, which may be comprised of hardware (e.g., circuitry, dedicated logic, programmable logic, microcode, etc.), software (such as instructions run on a processing device), firmware, or a combination thereof.

Effective ocular screening of cooperative examinees, such as adults, and non-cooperative examinees such as children or animals, may be achieved through the use of the vision screening device 100. The vision screening device 100 is configured to present attention-getting stimuli to an examinee. The presentation of attention-getting stimuli may be needed, particularly when screening non-cooperative examinees, in order to attract the examinees' direction of gaze. For proper ocular screening, the direction of gaze needs to be in the direction of lens component 102 coupled to image capture component 104.

Various types of attention-getting stimuli may be utilized. In one example, an auditory stimulus may be used. The auditory stimulus may be a digitally recorded soundtrack under computer program control in the vision screening device 100 and may be presented, for example, via the speaker 105. In another example, an unfocussed time-dynamic visual stimulus may be used. The visual stimulus may be presented through the use of colored LEDs provided, for example, by the LED array 106. In some examples, the visual stimulus from the LED array 106 can be used to minimize an accommodative response from examinees. Additional locations may also be used to produce a chromatic blur to further reduce eye accommodation.

The visual stimulus may be comprised of an arrangement of differently colored LEDs. The arrangement of colored LEDs produce light in the visible spectrum below 600 nanometers to avoid contamination of near infrared (NIR) LED stimulus. This configuration allows the visual stimulus to be presented for attention getting purposes, but not to be seen in recorded images. The visible LED stimulus is independent of NIR LED stimulus and is not used in the data analysis associated with determining refractive error or gaze direction.

An example arrangement of the LED array 106 can include visible LEDs 106a that are positioned between the NIR LEDs 106b and that are coplanar with NIR LEDs 106b. Light emitted by visible LEDs 106a can pass through the holographic diffuser 108, creating diffuse stimuli, and is reflected towards the examinee by the beam-splitter 110.

As with the auditory stimulus, the visible LEDs 106a may also be under computer program control in the vision screening device 100. More specifically, control parameters such as the intensity, duration, pattern, cycle time, and chromatic blur associated with the visible LEDs 106a may be under computer program control. With respect to intensity, the visible LEDs 106a must be regulated to be bright enough to attract the direction of an examinee, while at the same time being limited in brightness to avoid stimulating pupil constriction.

The duration of time in which the visible LEDs 106a are turned on before being turned off is measured in milliseconds and is regulated based on the brightness of the visible LEDs 106a. The visible LEDs 106a can be arranged in a pattern appearing as three concentric rings. In this arrangement, the three concentric rings appear to the examinee as centered in the image capture component 104 of the vision screening device 100. Each of the concentric rings may be comprised of more than one LED color spaced apart in a random pattern. A plurality of pattern combinations may be presented to an examinee in random order. The number of data frames collected prior to making a change to a pattern may also be regulated.

At least one objective of the control parameters associated with the visible LEDs 106a is to present diffuse, random, and rapidly changing visible light patterns to an examinee. Such patterns can reduce, and in some cases may inhibit, accommodation of the examinee's eyes at a focal distance that is preferably set at one (1) meter from image capture component 104. The focal distance can be determined using the range finder 112.

Presentation of a visual stimulus need not be limited to the use of the visible LEDs 106a arranged in the LED array 106. In alternate examples, visual stimulus can be provided by an external source independent of the vision screening device 100, an external source coupled to and under computer program control of the vision screening device 100, or other suitable combinations thereof. Regardless of the attention-getting mechanism employed, an attention-getting stimulus is preferably presented continuously throughout an ocular examination.

Figure 3:
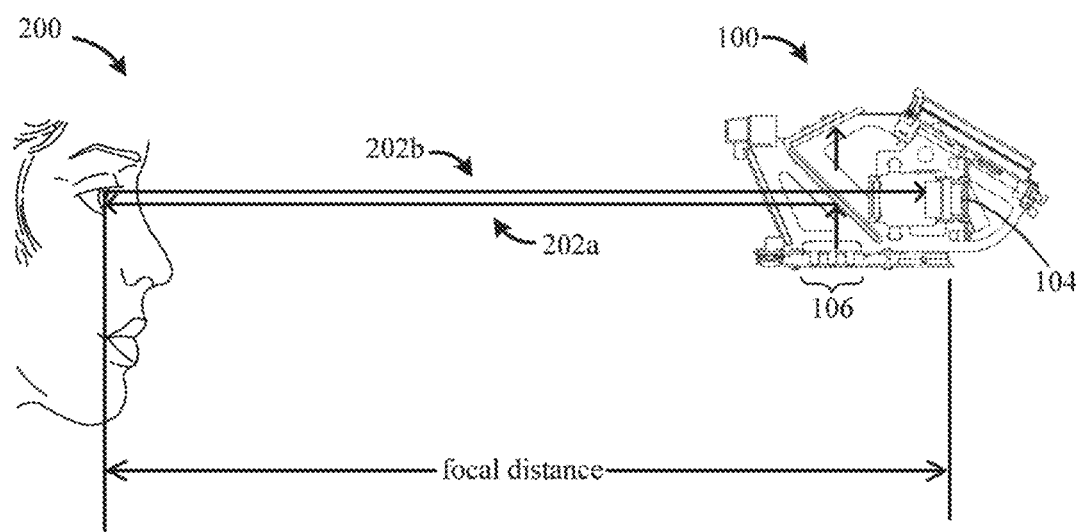
FIG. 3 illustrates emitted and reflected light paths between an examinee and the vision screening device of FIG. 1.

As illustrated in FIG. 3, light emitted from the LED array 106 is reflected by the beam-splitter 110 and transmitted in a direction 202a along the optical axis towards an examinee's eyes 200. Light reflected back and exiting the examinee's eyes 200 is returned in a direction 202b and received at the image capture component 104 of vision screening device 100. The light received by the image capture component 104 is used to generate images and data that can be analyzed to estimate the refractive error of the examinee's eyes 200.

The ability for young children to more easily accommodate their eyes may result in inaccurate refractive error estimates because when the eyes of the examinee are accommodated, the eyes will appear to a vision screener as requiring no optical correction. An advantage of displaying an imitation of chromatic aberration by the vision screening device 100 is that it can trick the examinee's eyes to reduce and/or eliminate eye accommodation, and thereby improve the accuracy of the refractive error estimates determined by the vision screening device 100.

Figure 4:
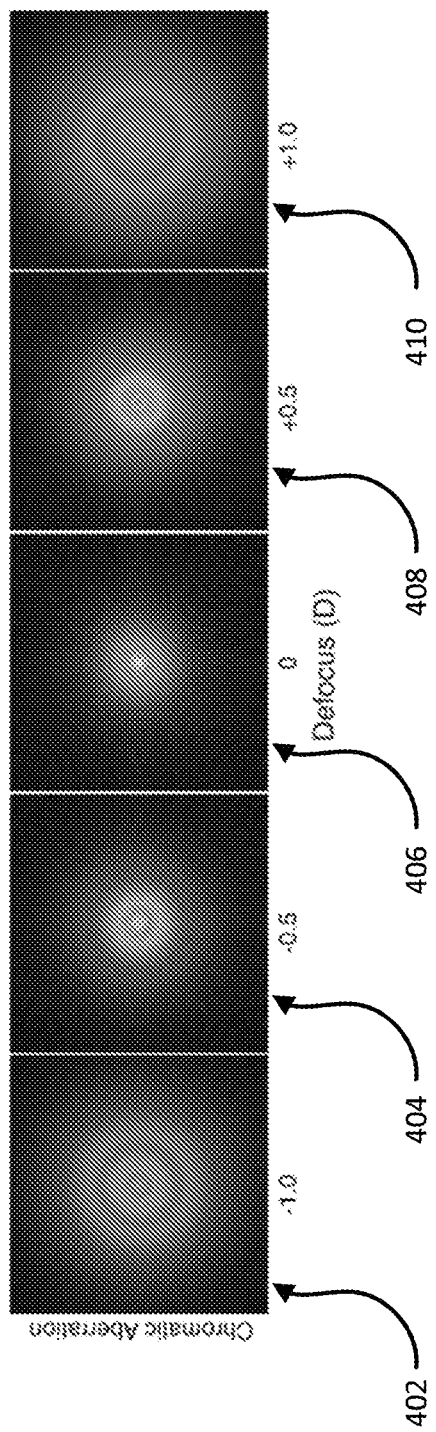
FIG. 4 illustrates examples of chromatic aberrations that can be displayed by the vision screening device of FIG. 1.

FIG. 4 illustrates example chromatic aberrations 402-410 that can be displayed by the vision screening device 100 to mitigate eye accommodation during a vision acuity exam. The chromatic aberrations 402-410 are presented as fringes of color along boundaries that separate dark and bright areas of an image. An examinee will not be consciously aware of the effect of the chromatic aberrations 402-410 on their eyes. Instead, the chromatic aberrations 402-410 will be interpreted by the examinee's brain as a defocus error of their eyes, which causes the brain to reflexively adjust their eyes to accommodate and correct the defocus error.

The vision screening device 100 imitates chromatic aberration to cause the examinee's eyes to be tricked into focusing or defocusing. For example, a chromatic aberration 402 can be displayed as a blurred fringe of visible blue light that surrounds a blurred core of visible red light. In some examples, a blurred ring of visible green light is displayed between the blurred fringe of visible blue light and blurred core of visible red light. In certain examples, the chromatic aberration 402 can be displayed by the vision screening device 100 to stimulate an examinee's eyes to defocus inwardly closer to the infinity focus to reduce accommodation, and thereby improve refractive error estimates by the vision screening device 100.

As another example, a chromatic aberration 410 can be displayed as a blurred fringe of visible red light that surrounds a blurred core of visible blue light. In some examples, a blurred ring of visible green light is displayed between the blurred fringe of visible red light and blurred core of visible blue light. The chromatic aberration 410 can be displayed by the vision screening device 100 to stimulate an examinee's eyes to focus outwardly.

The vision screening device 100 can display additional examples of chromatic aberrations 404-408 to produce a reflexive adjustment of an examinee's eyes, as desired. For example, a chromatic aberration 404 includes a blurred fringe of visible blue light that surrounds a blurred core of visible red light, and a blurred ring of visible green light between the blurred fringe of visible blue light and blurred core of visible red light. Thus, the chromatic aberration 404 is similar to the chromatic aberration 402. The chromatic aberration 404 differs from the chromatic aberration 402 in that the blue, red, and green colors are less diffused (i.e., less blurry). Thus, the accommodative effect from the chromatic aberration 404 is less than the accommodative effect from the chromatic aberration 402. As an illustrative example, the chromatic aberration 402 can produce an accommodative effective of −1.0 diopters, whereas the chromatic aberration 404 can produce an accommodative effective of −0.5 diopters.

A chromatic aberration 408 includes a blurred fringe of visible red light that surrounds a blurred core of visible blue light, and a blurred ring of visible green light between the blurred fringe of visible red light and blurred core of visible blue light. Thus, the chromatic aberration 408 is similar to the chromatic aberration 410. The chromatic aberration 408 differs from the chromatic aberration 410 in that the blue, red, and green colors are less diffused. Thus, the accommodative effect from the chromatic aberration 408 is less than the accommodative effect from the chromatic aberration 410. As an illustrative example, the chromatic aberration 410 can produce an accommodative effective of +1.0 diopters, whereas the chromatic aberration 408 can produce an accommodative effective of +0.5 diopters.

In some examples, the vision screening device 100 can display a chromatic aberration 406 that is neutral. For example, the chromatic aberration 406 does not cause an examinee's eyes to focus outwardly or defocus inwardly, but is rather displayed as an attention-getting stimulus. In some examples, the vision screening device 100 can transition back and forth between displaying various types of chromatic aberrations 402-410 during a vision acuity exam.

In some further examples, the vision screening device 100 can provide convergence control separate or in addition to mitigating eye accommodation during a vision acuity exam. Young children overlap images from each eye as a means to determine a distance to an object, and thereby to set a gaze angle to help with focusing and accommodating their eyes. The vision screening device 100 can display the chromatic aberrations 402-410 as separate objects that move relative to each other. In one example, the vision screening device 100 can display the chromatic aberrations 402-410 as separate objects that move toward each other, and that overlap or pass each other by. In further examples, the vision screening device 100 can display the chromatic aberrations 402-410 as alternating objects. Such techniques by the vision screening device 100 can provide additional effectiveness for accommodation control in younger children by causing eye focusing and accommodation further away from the device.

The chromatic aberrations 402-410 are displayed by an illumination component of the vision screening device 100. In some embodiments, the illumination component includes one or more of the visible LEDs 106a that generate the chromatic aberrations 402-410 which are reflected through the front window 116 and towards the examinee for viewing.

In alternative examples, the illumination component includes one or more of the visible LEDs 106a and a light guide that disperses visible light from the one or more visible LEDs 106a on the exterior of the housing 150 of the vision screening device 100. The light guide disperses the visible light from the one or more visible LEDs 106a to at least partially surround the exterior of the housing 150, and thereby display the chromatic aberrations 402-410. In some examples, the light guide disperse the visible light along the bottom of the housing 150, along the sides of the housing 150, along the top of the housing 150, or entirely around the housing 150.

In some examples, the light dispersed by the light guide around the exterior of the housing 150 is a blurred fringe of visible blue light. In some examples, one or more visible LEDs 106a display a blurred core of visible red light through the front window 116 and towards the examinee, while the light guide disperses the blurred fringe of visible blue light around the exterior of the housing 150 to resemble the chromatic aberration 402, and thereby to stimulate the examinee's eyes to defocus inwardly closer to the infinity focus.

In some further examples, the light dispersed by the light guide around the exterior of the housing 150 is a blurred fringe of visible red light. In some examples, one or more visible LEDs 106a display a blurred core of visible blue light through the front window 116 and towards the examinee, while the light guide disperses the blurred fringe of visible red light around the exterior of the housing 150 to resemble the chromatic aberration 410, and thereby to stimulate the examinee's eyes to focus outwardly.

In some further examples, the light dispersed by the light guide around the exterior of the housing 150 can transition back and forth between a blurred fringe of visible blue light and a blurred fringe of visible red light. Additional examples are contemplated. Thus, the visible LEDs 106a are controllable to generate the chromatic aberrations 402-410 to reduce, and in some cases eliminate accommodation of the examinee's eyes to improve refractive error estimates determined from the images and data captured by the vision screening device 100.

In addition, the vision screening device 100 can use the chromatic aberrations 402-410 produced by the visible LEDs 106a to control and measure eye accommodation. The eye accommodation measurements can be used to diagnose and assess presbyopia, which is a gradual, age-related loss of the eyes' ability to focus actively on nearby objects. Thus, the vision screening device 100 can also be used to diagnose and measure presbyopia in older adults.

Figure 5:
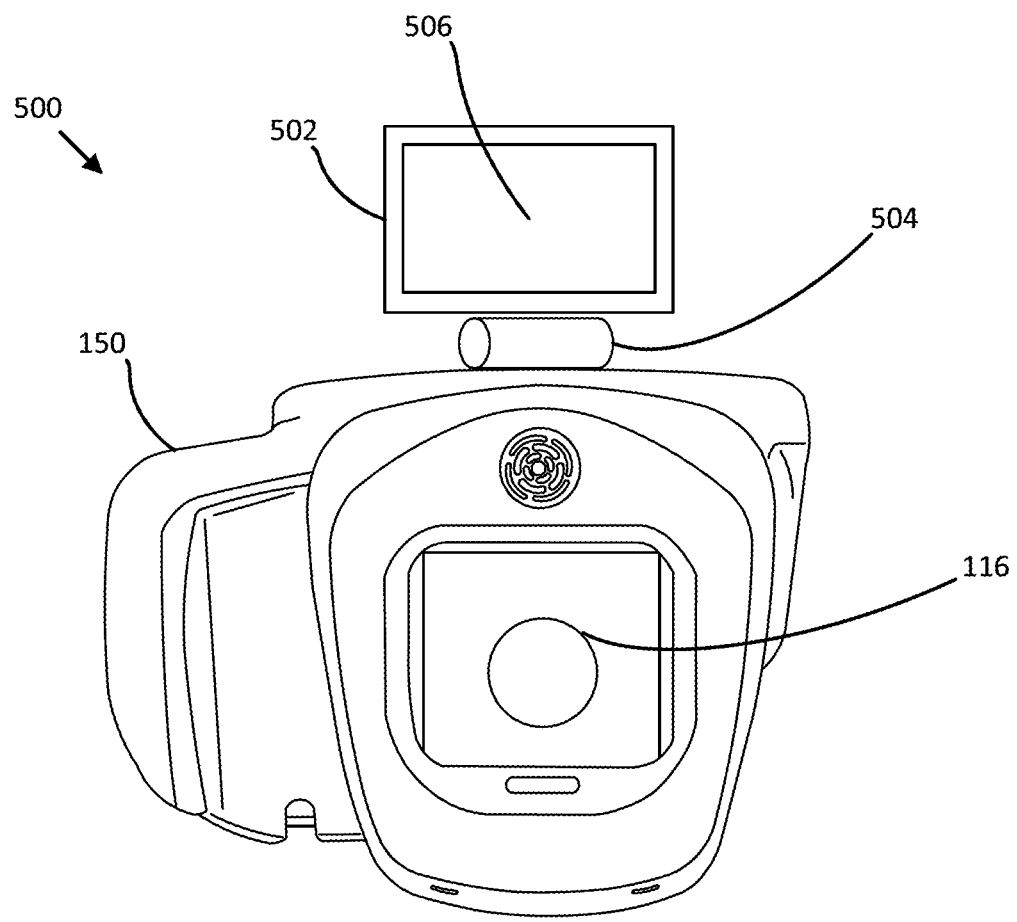
FIG. 5 illustrates another example embodiment of the vision screening device that includes a display unit attached to a housing of the vision screening device.

FIG. 5 illustrates another example of a vision screening device 500 that is configured in a manner similar to that of the vision screening device 100. The vision screening device 500 includes a display unit 502 attached to the housing 150 by a pivot 504. The display unit 502 can rotate about the pivot 504 to move from a stowed position to a deployed position. In some examples, the display unit 502 can be manually rotated about the pivot 504 such as by the hand of a user who is operating the vision screening device 500. Alternatively, an electronic motor can be used to move the display unit 502 between the stored and deployed positions in response to a selection of a user input on the operator display screen 114 or elsewhere on the housing 150.

In FIG. 5, the display unit 502 is shown in the deployed position from the perspective of the examinee's eyes such that the front window 116 faces the examinee's eyes. In this illustrative example, the display unit 502 is attached to the top of the housing 150. Alternatively, the display unit 400 can be attached to one of the sides or to the bottom of the housing 150.

The display unit 502 includes a liquid-crystal display (LCD) 506 as the illumination component. When in the deployed position, the LCD 506 faces the examinee's eyes such that at least one of the chromatic aberrations 402-410 can be displayed on the LCD 506 for viewing by the examinee's eyes during a vision acuity examination to reduce eye accommodation.

The display unit 502 can display the chromatic aberrations 402-410 as separate objects that move relative to each other, and that possibly overlap or pass each other by. Alternatively, the display unit 502 can display the chromatic aberrations 402-410 as alternating objects. This can help produce focusing and accommodation further away from the device, and may provide convergence control and additional effectiveness for accommodation control.

Figure 6:
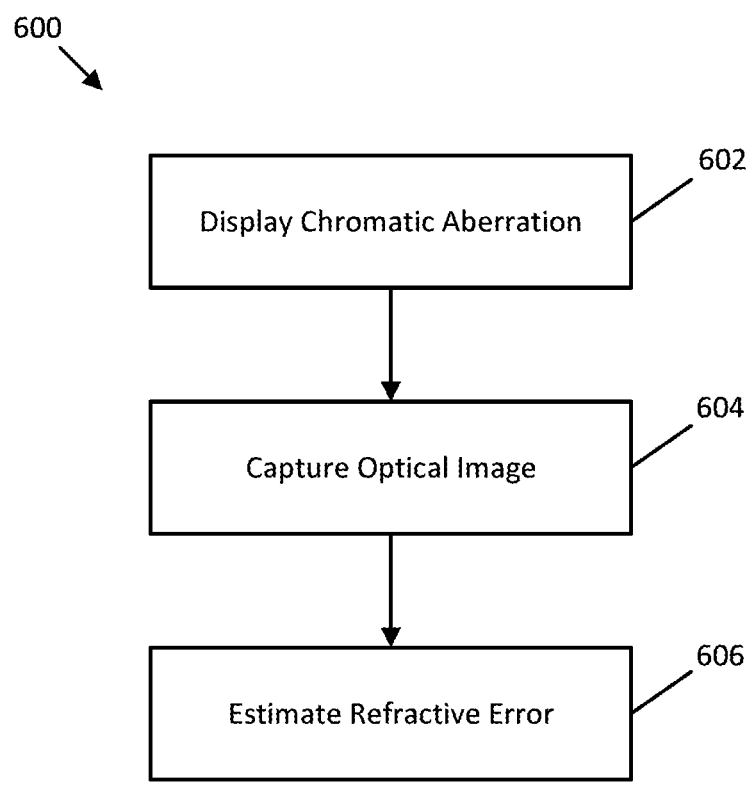
FIG. 6 illustrates an example of a method of estimating refractive error of an examinee's eyes using the vision screening device of FIG. 1 or FIG. 5.

FIG. 6 illustrates a method 600 of estimating refractive error of an examinee's eyes using the vision screening device 100 (or 500). The method 600 includes an operation 602 of displaying a chromatic aberration, followed by an operation 604 of capturing an optical image, and followed by an operation 606 of estimating refractive error. In some examples, operations 602-606 are automatically performed when a user of the vision screening device 100 selects a predetermined workflow that is selectable by one or more user input on the operator display screen 114 or elsewhere on the housing 150 of the vision screening device 100.

In operation 602, displaying the chromatic aberration includes displaying at least one of the chromatic aberrations 402-410 shown in FIG. 4, as described above. For example, operation 602 includes displaying the chromatic aberration 402 as a blurred fringe of visible blue light that surrounds a blurred core of visible red light to stimulate an examinee's eyes to defocus inwardly closer to the infinity focus, thereby reducing or eliminating eye accommodation.

In some examples, operation 602 includes displaying the chromatic aberration 410 as a blurred fringe of visible red light that surrounds a blurred core of visible blue light to stimulate an examinee's eyes to focus outwardly. In some further examples, operation 602 includes displaying one or more of the chromatic aberrations 402-410, such that operation 602 can transition back and forth between displaying the chromatic aberrations 402-410.

Operation 602 can be performed by any one of the configurations of the vision screening device 100, 500 described above. For example, displaying the chromatic aberration in operation 602 can be performed by one or more of the visible LEDs 106a that generate the chromatic aberration for viewing through the front window 116. Alternatively, displaying the chromatic aberration in operation 602 can be performed by a light guide that disperses visible light generated from the one or more visible LEDs 106a to at least partially surround the exterior of the housing 150. In further examples, displaying the chromatic aberration in operation 602 can be performed by the LCD 506 attached to the housing 150 of the vision screening device 500.

Operation 604 is performed by the image capture component 104 of the vision screening device 100. The image capture component 104 captures one or more optical images. In some examples, the image capture component 104 captures a plurality of optical images.

The image capture component 104 can capture the optical images a predetermined period of time after the chromatic aberration is displayed in operation 602. In some examples, the image capture component 104 captures the optical images simultaneously while the chromatic aberration is being displayed by the illumination component.

In examples where operation 602 transitions back and forth between displaying the chromatic aberrations 402-410, operation 604 can include capturing a plurality of optical images during the transition, and tagging or time-stamping each captured optical image. The tags or time-stamps can be used to associate each captured image with the chromatic aberration 402-410 that was being displayed by the vision screening device 100.

With respect to operation 606, refractive error is defined as the optical correction that would provide good vision. Operation 606 can be performed according to any of the methods and techniques, including the use of algorithms, described in U.S. Pat. No. 9,237,846 issued on Jan. 19, 2016, and U.S. Pat. No. 9,408,535 issued on Aug. 9, 2016, the entireties of which are hereby incorporated by reference.

In examples where operation 602 transitions back and forth between displaying the chromatic aberrations 402-410 and operation 604 includes capturing a plurality of optical images during the transition, the method 600 can include an additional operation of determining a level of eye accommodation based on the captured plurality of optical images. For example, the ability of an examinee to accommodate their eyes based on the chromatic aberrations 402-410 that are displayed by the vision screening device 100 can be determined and quantified as a score that is displayed on the operator display screen 114 of the vision screening device 100. In some examples, the score can be used to diagnose and assess presbyopia in older adult patients.

In some examples, the method 600 can include further operations of displaying the chromatic aberrations 402-410 as separate objects that move relative to each other. In one example, the method 600 can include displaying the chromatic aberrations 402-410 as separate objects that move toward each other, and that overlap or pass each other by. Alternatively, the method 600 can include displaying the chromatic aberrations 402-410 as alternating objects. These further operations can help produce eye focusing and accommodation further away from the vision screening device 100, and can provide convergence control and additional effectiveness for eye accommodation control in younger children.

FIG. 7 schematically illustrates example components of the vision screening device 100. The vision screening device 500 can be similarly configured. As shown in FIG. 7, the vision screening device 100 has a processing device 702, a system memory 708, and a system bus 720 coupling the system memory 708 to the processing device 702. The processing device 702 is an example of a processor such as a central processing unit (CPU). The processing device 702 is operatively connected to at least the image capture component 104 and the illumination component of the vision screening device 100.

The system memory 708 is an example of a computer readable data storage device that stores software instructions that are executable by the processing device 702. The system memory 708 includes a random-access memory ("RAM") 710 and a read-only memory ("ROM") 712. Input/output logic containing the routines to transfer data between elements within the vision screening device 100, such as during startup, is stored in the ROM 712.

The vision screening device 100 can also include a mass storage device 714 that is able to store software instructions and data. The mass storage device 714 is connected to the processing device 702 through a mass storage controller (not shown) connected to the system bus 720. The mass storage device 714 and its associated computer-readable data storage medium provide non-volatile, non-transitory storage for the vision screening device 100.

Although the description of computer-readable data storage media contained herein refers to a mass storage device, it should be appreciated by those skilled in the art that computer-readable data storage media can be any available non-transitory, physical device or article of manufacture from which the device can read data and/or instructions. The mass storage device 714 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The vision screening device 100 may operate in a networked environment using logical connections to remote network devices through the network 20. The vision screening device 100 connects to the network 20 through a network interface unit 704 connected to the system bus 720. The network interface unit 704 may also be utilized to connect to other types of networks and remote computing systems.

The vision screening device 100 can also include an input/output controller 706 for receiving and processing input from a number of input devices. Similarly, the input/output controller 706 may provide output to a number of output devices.

The mass storage device 714 and the RAM 710 can store software instructions and data. The software instructions can include an operating system 718 suitable for controlling the operation of the device. The mass storage device 714 and/or the RAM 710 also store software instructions 716, that when executed by the processing device 702, cause the device to provide the functionalities discussed in this document.

The various embodiments described above are provided by way of illustration only and should not be construed to be limiting in any way. Various modifications can be made to the embodiments described above without departing from the true spirit and scope of the disclosure.

What is claimed is:

1. A vision screening device, comprising:
   a housing defining a front window;
   an image capture component positioned inside the housing;
   an illumination component positioned inside the housing, the illumination component having one or more light-emitting diodes;
   at least one processing device operatively connected to the image capture component and the illumination component; and
   at least one computer readable data storage device storing software instructions that, when executed by the at least one processing device, cause the vision screening device to:
   control the illumination component to display a chromatic aberration through the front window of the housing, the chromatic aberration being displayed as fringes of color along boundaries that separate dark and bright areas of an image;
   capture an optical image of an examinee's eyes using the image capture component during the display of the chromatic aberration; and
   estimate a refractive error of one or both of the examinee's eyes based on the optical image captured by the image capture component.

2. The device of claim 1, wherein the chromatic aberration is a blurred fringe of visible blue light that surrounds a blurred core of visible red light.

3. The device of claim 1, wherein the chromatic aberration is a blurred fringe of visible red light that surrounds a blurred core of visible blue light.

4. The device of claim 1, wherein the software instructions, when executed by the at least one processing device, further cause the vision screening device to:
   display chromatic aberrations as separate objects that move relative to each other to provide convergence control.

5. The device of claim 1, wherein the software instructions, when executed by the at least one processing device, further cause the vision screening device to:
   display a plurality of chromatic aberrations;
   capture a plurality of optical images;
   tag each optical image of the plurality of optical images for an association with at least one chromatic aberration of the plurality of chromatic aberrations;
   determine a score quantifying eye accommodation; and
   use the score to diagnose presbyopia.

6. A method of vision screening, comprising:
   displaying a chromatic aberration as fringes of color along boundaries that separate dark and bright areas of an image, the chromatic aberration being displayed by control of one or more light-emitting diodes;
   capturing an optical image of one or more eyes during the display of the chromatic aberration; and
   estimating a refractive error of the one or more eyes based on the optical image.

7. The method of claim 6, wherein the chromatic aberration is a blurred fringe of visible blue light that surrounds a blurred core of visible red light.

8. The method of claim 6, wherein the chromatic aberration is a blurred fringe of visible red light that surrounds a blurred core of visible blue light.

9. The method of claim 6, further comprising:
   displaying chromatic aberrations as separate objects that move relative to each other to provide convergence control.

10. The method of claim 6, further comprising:
    displaying a plurality of chromatic aberrations;
    capturing a plurality of optical images;
    tagging each optical image of the plurality of optical images for an association with at least one chromatic aberration of the plurality of chromatic aberrations;
    determining a score quantifying eye accommodation; and
    using the score to diagnose presbyopia.

11. A non-transitory computer-readable data storage medium comprising software instructions that, when executed by a processing device of a vision screening device, cause the processing device of the vision screening device to:
    display a chromatic aberration as fringes of color along boundaries that separate dark and bright areas of an image, the chromatic aberration being displayed by control of one or more light-emitting diodes;
    capture an optical image of one or more eyes during the display of the chromatic aberration; and
    estimate a refractive error of the one or more eyes based on the optical image.

12. The non-transitory computer-readable data storage medium of claim 11, wherein the chromatic aberration is a blurred fringe of visible blue light that surrounds a blurred core of visible red light.

13. The non-transitory computer-readable data storage medium of claim 11, wherein the chromatic aberration is a blurred fringe of visible red light that surrounds a blurred core of visible blue light.

14. The non-transitory computer-readable data storage medium of claim 11, wherein the software instructions further cause the processing device of the vision screening device to:
   display chromatic aberrations as separate objects that move relative to each other to provide convergence control.

15. The non-transitory computer-readable data storage medium of claim 11, wherein the software instructions further cause the processing device of the vision screening device to:
   display a plurality of chromatic aberrations;
   capture a plurality of optical images;
   tag each optical image of the plurality of optical images for an association with at least one chromatic aberration of the plurality of chromatic aberrations;
   determine a score quantifying eye accommodation; and
use the score to diagnose presbyopia.

* * * * *